US011321372B2

(12) United States Patent
Jacobs et al.

(10) Patent No.: US 11,321,372 B2
(45) Date of Patent: May 3, 2022

(54) METHOD AND SYSTEM FOR A NATURAL LANGUAGE PROCESSING USING DATA STREAMING

(71) Applicant: THE JOHNS HOPKINS UNIVERSITY, Baltimore, MD (US)

(72) Inventors: Michael Jacobs, Baltimore, MD (US); Vladimir Braverman, Baltimore, MD (US); Nikita Ivkin, Baltimore, MD (US); Sanghyun Choi, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 532 days.

(21) Appl. No.: 15/845,842

(22) Filed: Dec. 18, 2017

(65) Prior Publication Data

US 2018/0189384 A1    Jul. 5, 2018

Related U.S. Application Data

(60) Provisional application No. 62/441,619, filed on Jan. 3, 2017.

(51) Int. Cl.
*G06F 16/33*        (2019.01)
*G06F 16/36*        (2019.01)
*G16H 10/60*        (2018.01)
*G16H 15/00*        (2018.01)
*G16H 30/20*        (2018.01)
(Continued)

(52) U.S. Cl.
CPC .......... *G06F 16/3344* (2019.01); *G06F 16/36* (2019.01); *G16H 10/60* (2018.01); *G16H 15/00* (2018.01); *G16H 30/20* (2018.01); *G16H 50/20* (2018.01); *G16H 50/30* (2018.01)

(58) Field of Classification Search
CPC ...... G06F 16/3344; G06F 16/36; G16H 10/60
See application file for complete search history.

(56) References Cited

U.S. PATENT DOCUMENTS 9,135,242 B1 *   9/2015  Wang ...................... G06F 40/30
9,208,217 B2    12/2015  Milward et al.
2002/0147724 A1 * 10/2002 Fries ..................... G06F 16/951
(Continued)

OTHER PUBLICATIONS

Charikar et al., "Finding Frequent Items in Data Streams," date unknown, 11 pages.
(Continued)

*Primary Examiner* — Syed H Hasan
*Assistant Examiner* — Anthony G Gemignani
(74) *Attorney, Agent, or Firm* — MH2 Technology Law Group LLP

(57) ABSTRACT

System and methods for obtaining frequent terms in a set of data is provided. The method comprises obtaining the set of data comprising a stream of terms; analyzing the stream of terms using a modified data streaming generator to find a set of frequent terms; forming a dictionary of terms based on the set of most frequent terms; identifying one or more of the set of frequent terms in the set of data; and analyzing the one or more of the set of frequent terms in the set of data to determine a context and/or structure based on neighboring terms in the set of data; providing a visualization tool for the interactions with the frequent terms and the application at hand.

16 Claims, 5 Drawing Sheets

(51) Int. Cl.
*G16H 50/20* (2018.01)
*G16H 50/30* (2018.01)

(56) References Cited

U.S. PATENT DOCUMENTS

| | | | | |
|---|---|---|---|---|
| 2008/0288537 | A1* | 11/2008 | Golovchinsky | G06F 16/41 |
| 2010/0332287 | A1* | 12/2010 | Gates | G06Q 30/0203 |
| | | | | 705/7.32 |
| 2012/0310863 | A1* | 12/2012 | Crockett | G06N 5/046 |
| | | | | 706/12 |
| 2013/0253910 | A1* | 9/2013 | Turner | G06F 40/253 |
| | | | | 704/9 |
| 2014/0006926 | A1 | 1/2014 | Vijaykalyan et al. | |
| 2015/0325133 | A1* | 11/2015 | Gaglani | G09B 7/00 |
| | | | | 434/322 |
| 2016/0085849 | A1* | 3/2016 | Gallivan | G06F 16/283 |
| | | | | 707/737 |
| 2016/0147878 | A1* | 5/2016 | Mana | G06F 16/3344 |
| | | | | 707/706 |
| 2016/0148374 | A1* | 5/2016 | Sevenster | G06F 19/321 |
| | | | | 382/131 |
| 2016/0328386 | A1* | 11/2016 | Cross, III | G06F 40/30 |

OTHER PUBLICATIONS

Goyal et al., "Sketch Algorithms for Estimating Point Queries in NLP," date unknown, 11 pages.

Goyal et al., "Sketching Techniques for Large Scale NLP," Proceedings of the NAACL HLT 2010 Sixth Web as Corpus Workshop, pp. 17-25, Jun. 2010.

Goyal et al., "Streaming for Large Scale NLP: Language Modeling," University of Utah, School of Computing, date unknown, 9 pages.

* cited by examiner

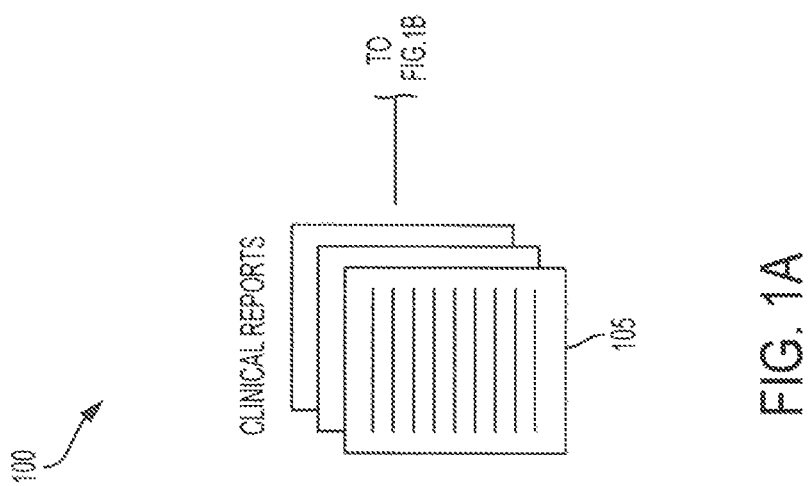

METHOD AND SYSTEM FOR A NATURAL LANGUAGE PROCESSING USING DATA STREAMING

CROSS REFERENCE TO RELATED APPLICATIONS

This application claims the benefit of, and relies on the filing date of U.S. Provisional Application No. 62/441,019, filed on Jan. 3, 2017, the entire disclosure of which is incorporated herein by reference.

FIELD

The present disclosure relates generally to systems and methods for natural language processing (NLP), and more particularly to systems and methods for NLP using a modified data streaming algorithm based on the data streaming algorithm called DreamNIP.

BACKGROUND

Extracting information from electronic reports, such as clinical reports in the form of electronic medical records (EMR) or electronic health records (EHR), financial reports, and scientific reports is a challenging task since it requires a strong prior knowledge of the reports. For example, EHRs play a role as useful source of important medical data to clinicians. However, to extract and collect data or terms across medical records is a difficult task. There are NLP tools that aid in information extraction, but these methods can be computationally and memory intensive. Moreover, some NLP programs only provide extracted terms and it may be difficult to build quantitative relationships between these terms and what is in the report. With the growing number of reports, such knowledge is increasingly challenging to obtain in a quick and efficient manner.

In addition, it can be difficult to know which set of data could potentially be obtained from the reports without a strong prior knowledge of their contents. One of the simplest ways to gain a basic understanding of large corpora of text is to observe and extract the frequently occurring terms within the reports. For example, word clouds, consisting of frequent terms, are often effective in visually summarizing particular texts. Yet, finding frequent terms from large corpora is a challenging task by itself since every unique term in the data has to be stored in memory if approached in a naïve way.

Thus, a heretofore unaddressed need exists in the industry to address the aforementioned deficiencies and inadequacies.

SUMMARY

According to examples of the present teachings, a method of obtaining frequent terms in a set of data is provided. The method comprises obtaining the set of data comprising a stream of terms; analyzing the stream of terms using a modified data streaming generator to find a set of frequent terms; forming a dictionary of terms based on the set of frequent terms; identifying one or more of the set of frequent terms in the set of data; and analyzing the one or more of the set of frequent terms in the set of data to determine a context and/or structure based on neighboring terms in the set of data.

According to examples of the present teachings, a system is provided. The system comprises one or more processors; and a memory system comprising one or more non-transitory computer-readable media storing instructions that, when executed by at least one of the one or more processors, cause the one or more processors to perform a method of obtaining frequent terms in a set of data, the method comprising: obtaining the set of data comprising a stream of terms; analyzing the stream of terms using a modified data streaming generator to find a set of frequent terms; forming a dictionary of terms based on the set of frequent terms; identifying one or more of the set of frequent terms in the set of data; and analyzing the one or more of the set of frequent terms in the set of data to determine a context and/or structure based on neighboring terms in the set of data.

According to examples of the present teachings, a non-transitory computer readable storage medium is provided that comprises instructions for causing one, or more processors to perform a method of obtaining frequent terms in a set of data, the method comprising: obtaining the set of data comprising a stream of terms; analyzing the stream of terms using a modified data streaming generator to find a set of frequent terms; forming a dictionary of terms based on the set of frequent terms; identifying one or more of the set of frequent terms in the set of data; and analyzing the one or more of the set of frequent terms in the set of data to determine a context and/or structure based on neighboring terms in the set of data.

In some examples, a term from the stream of terms comprise a single word or a sequential set of words.

In some examples, the set of data comprises data from one or more data sources.

In some examples, subsequent to the obtaining, the method further comprises converting the stream of terms into a plurality of input vectors by the modified data streaming generator.

In some examples, subsequent to the converting the stream of terms, the method further comprises converting the plurality of input vectors into a corresponding plurality of sketch feature vectors by the data streaming generator, wherein each of the plurality of sketch feature vectors has a number of output dimensions that is less than a number of dimensions of a corresponding one of the input vectors.

In some examples, the method further comprises determining Shannon entropy to evaluate a distribution of the terms across the set of data.

In some examples, the method further comprises generating a multidimensional histogram to show interrelationships between terms of the stream of terms.

In some examples, the method further comprises generating a multidimensional graphic visualization tool for visualizing the stream of terms.

In some examples, the analyzing the stream of terms, further comprises parsing the set of data to identify syntactic relations, sematic relations, or both between terms.

In some examples, the set of data comprises a scientific or financial corpus of data.

In some examples, the analyzing the stream of terms, further comprises extracting negations and determining a structure surrounding the negation.

In some examples, the method further comprises testing a entropy or mutual information of each term in the stream of terms that was parsed in relationship to a frequency, a position, and importance.

In some examples, the method further comprises storing the one or more of the set of frequent terms in a data store for further analysis.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate the present disclosure and together with the description, serve to explain the principles of the present disclosure.

FIGS. 1A-1C show a process flow for a medical example, and in particular a breast cancer evaluation, according to examples of the present disclosure.

Figure 1B:
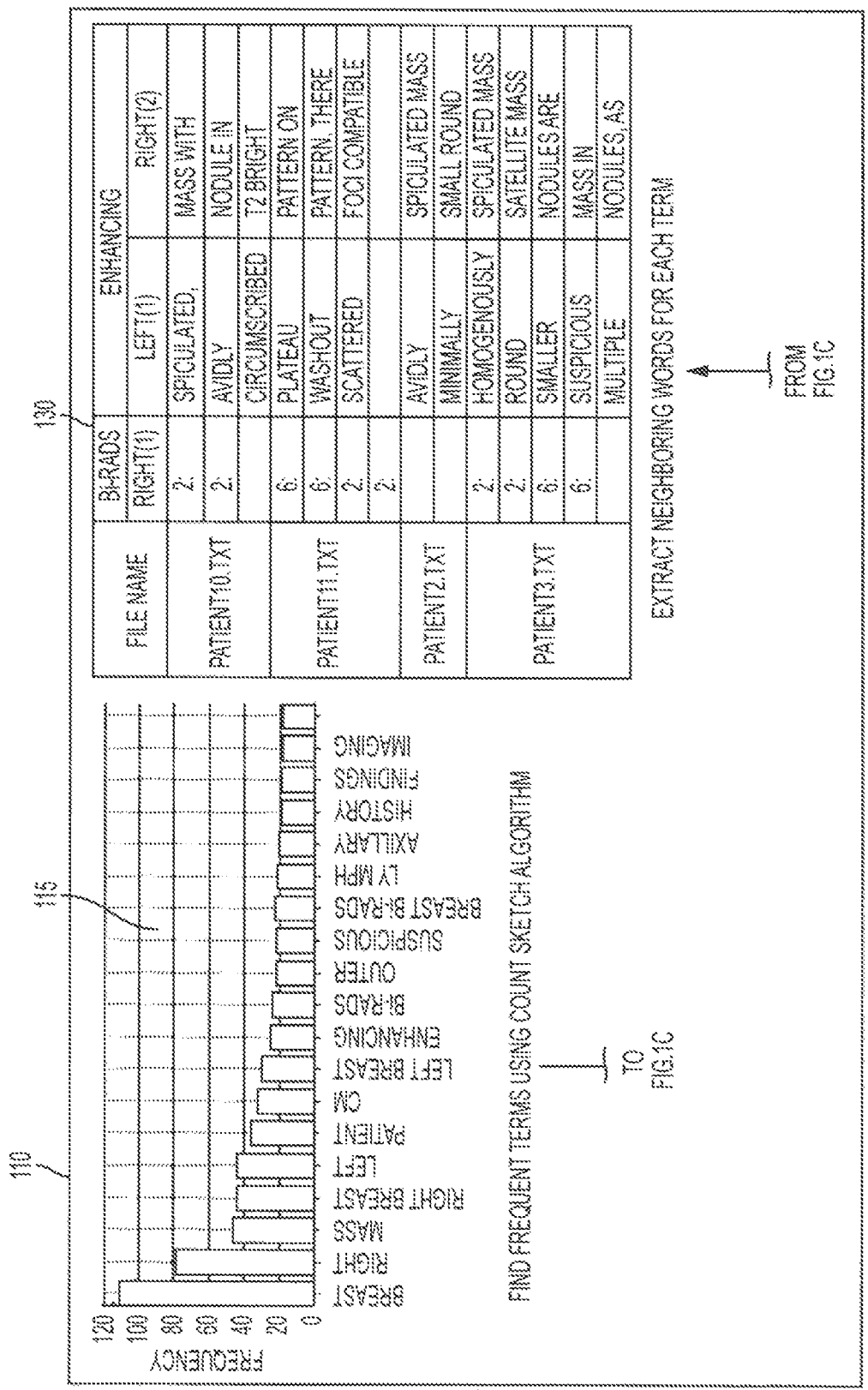

Reference will now be made in detail to exemplary implementations of the present disclosure, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific, exemplary implementations in which the present disclosure may be practiced. These implementations are described in sufficient detail to enable those skilled in the art to practice the present disclosure and it is to be understood that other implementations may be utilized and that changes may be made without departing from the scope of the present disclosure. The following description is, therefore, merely exemplary.

Generally speaking, examples of the present disclosure are directed to a method, system, and computer-readable medium to analyze large sets of data, from a data source using a NLP processing decision support system based on a data streaming algorithm, DSA, called DreamNLP. The data source can include, but are not limited to, financial statements (i.e., yearly reports, quarterly reports, income statements, cash flow statements, statements of changes in equity, etc.), clinical reports (i.e., EMR, EHR), scientific papers, etc. The DSA solves the problem of finding top-k most frequent items in data stream. Compared to naïve approach to this problem which implies keeping track of each item's frequency, DREAMNLP requires relatively low memory, therefore has less complexity than other NLP algorithms. Although it is a randomized approximate algorithm, it outputs good approximation with nigh probability, approximation level and probability of success can be controlled via input parameters.

By using the examples of the present disclosure, a dictionary of frequently occurring terms or phrases is generated in the data source using a low computational memory compared to conventional naïve counting approach other NLP programs use. The dictionary of frequency occurring terms can then serve as a basis set for an information extraction strategy. The distribution of these words is then evaluated across different sets of data from the data source using quantitative metrics. These metrics allow a better understanding of the words or phrases within the sets of data by tracing back the terms of interest to their actual usage in the sets of data. Shannon entropy is used to quantitatively evaluate how well the terms in the dictionary are distributed across all the sets of data. Other types of suitable entropy calculation can also be used. The words or phrases can be visualized in multi-dimensions to better determine the relationships between each object terms, reports, frequencies). To better assess whether a term is associated with extractable data, the terms can then be traced back to some of the sets of data they belong to and observe their context. The sets of data can then be annotated based on the analysis.

Figure 1C:
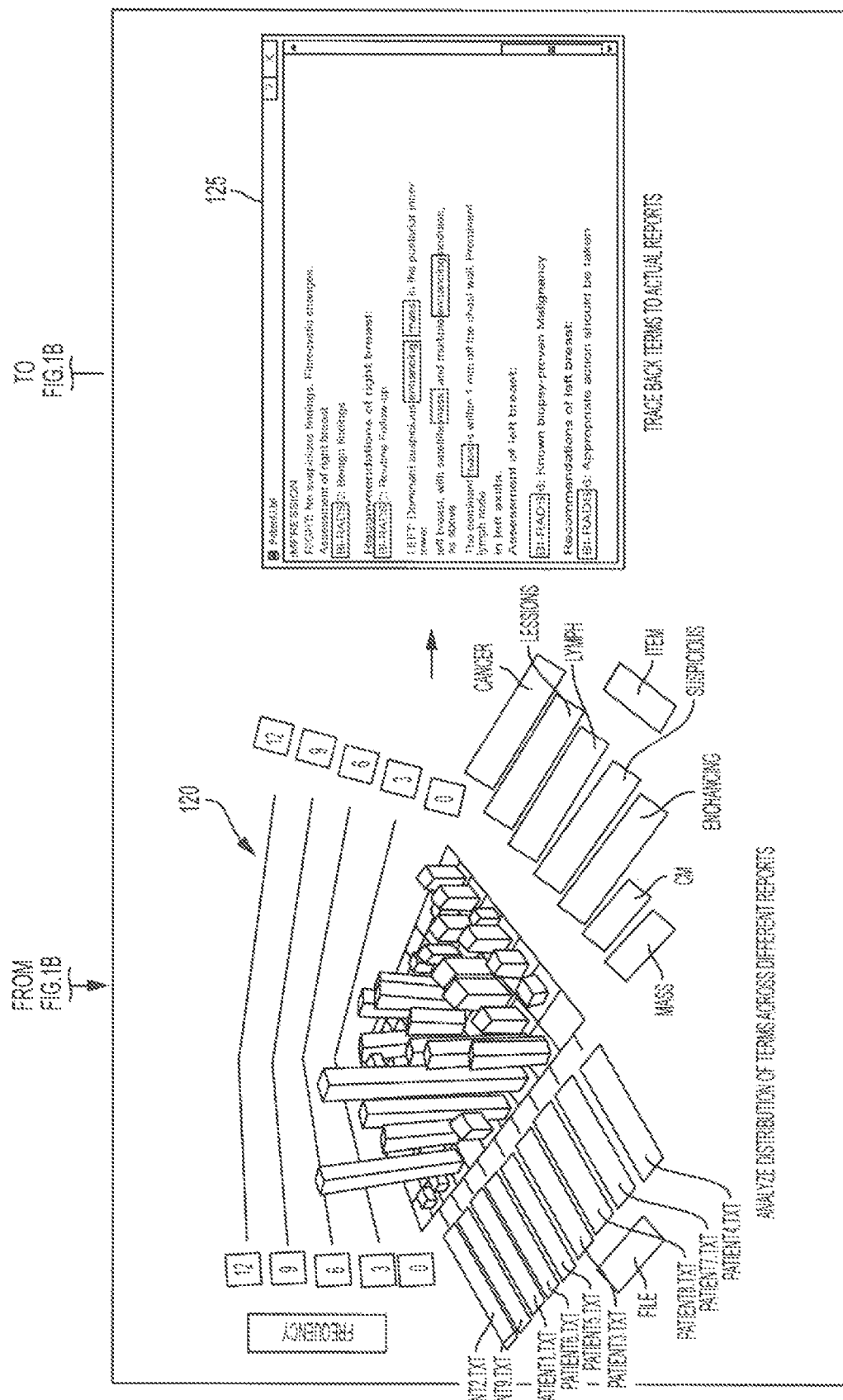

FIGS. 1A-1C shows a process flow 100 for a medical example, and in particular a breast cancer evaluation, according to examples of the present disclosure. However, as discussed above, other types of data can be examined using the examples of the present disclosure. At 105, the system 110, using the NLP processing decision support system based on a data streaming algorithm as disclosed herein, obtains a set of data from a data source (i.e., electronic data store). The set of data comprises a stream of terms. Depending on the context of use, the data source can be related to specific area of interest, such as financial, scientific, etc. in the financial example, the set of data can be different financial statements (i.e., yearly reports, quarterly reports, income statements, cash flow statements, statements of changes in equity, etc.). In the scientific example, the set of data can be different medical, e.g., clinical, reports (i.e., BAR or paper medical records for patent/family history, test results, imaging results, etc.)

In some examples, subsequent to the obtaining the set of data, the stream of terms is converted into a plurality of input vectors by a data streaming generator that performs the DREAMNLP, Subsequent to the converting the stream of terms, the plurality of input vectors are converted into a corresponding plurality of sketch feature vectors by the data streaming generator, wherein each of the plurality of sketch feature vectors has a number of output dimensions that is less than a number of dimensions of a corresponding one of the input vectors.

In terms of clinical reports, but also more broadly, these reports often contain detailed information that can be used for studying connections between different reports. In particular for EMR and HER reports, these reports contain snapshots of a patients' health that could be used for studying the "hidden" connections to a particular disease. For example, a clinician, by analyzing these reports in according with the present disclosure, can assist in determining whether a heart failure or a genetic risk for diabetes can be identified.

Figure 2:
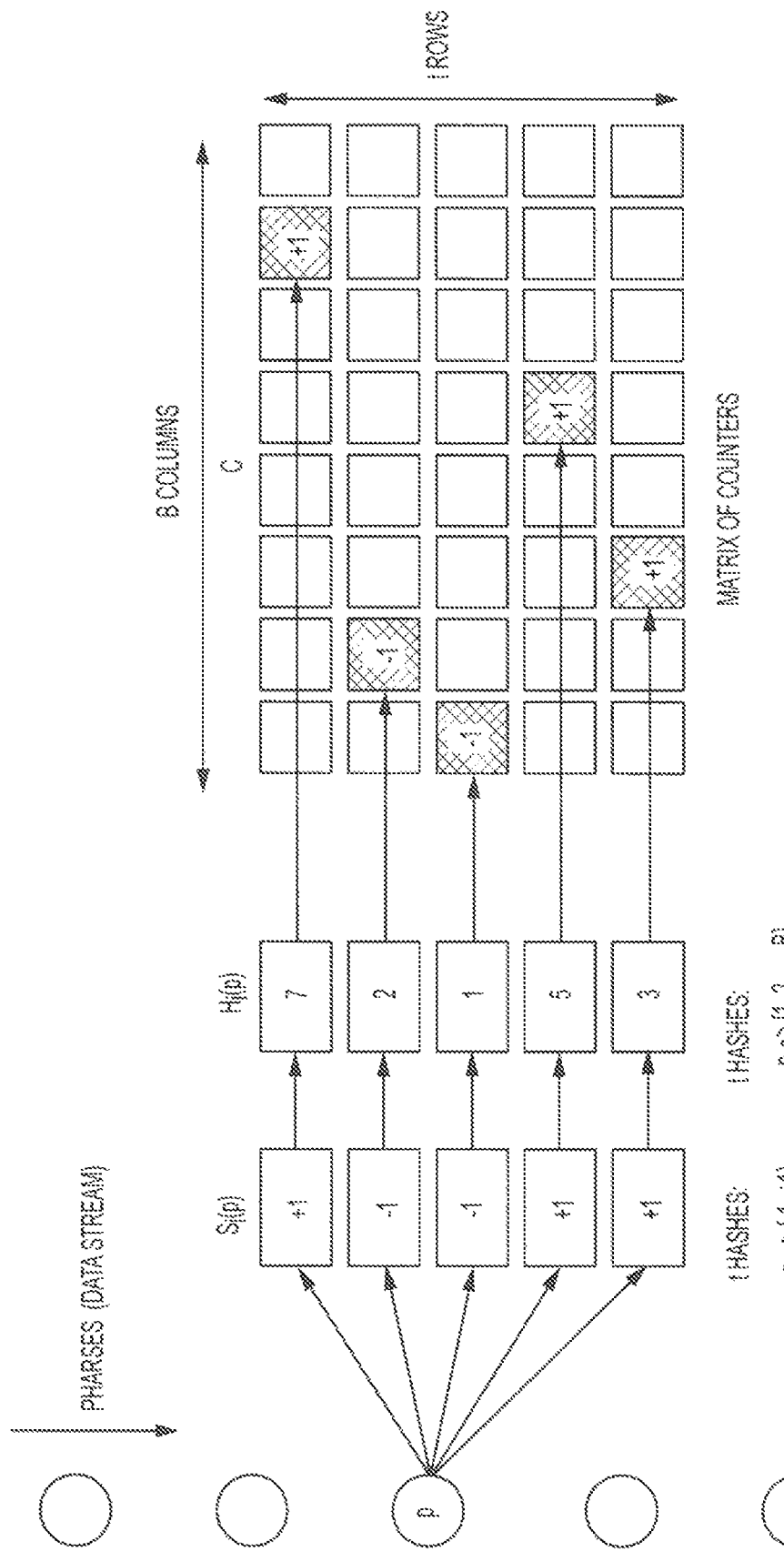
FIG. 2 is an illustration of a scheme for Count Sketch data structure, C, based on hash functions h and s applied to each item o, in the data stream.

Theoretically, sets of data (i.e., report(s)) can be viewed as a data stream of terms (a "term" could mean a single word or a sequential set of words). The top-k most frequent terms (i.e. heavy hitters) are found using a data streaming algorithm (DSA) with very low memory usage. As shown in FIG. 2 the DSA is a t☐b matrix C counters that can be viewed as t hash tables with b buckets for each hash table. For a particular choice of k, the parameters t and b play an important role in determining the accuracy of estimated frequencies. Now, suppose we have a stream of items $\{o_1, \ldots, o_n\}$, where n is the total number of items in the data stream. Also, let $\{h_1, \ldots, h_t\}$ and $\{s_1, \ldots, s_t\}$ be two sets of t hash functions that map $o_i$ to a particular value in $\{1, \ldots, b\}$ and $\{-1, 1\}$, respectively, where a is some l-th item in the stream. The DSA involves two operations:

Updating counters: For each i-th row in matrix C, update counter in $h_i(o_i)$-th column by adding $s_i(o_i)$. Estimating frequency; For each i-th row in matrix C, compute $C_{ij} \cdot s_i(o_i)$, where $j=h_i(o_i)$ as above, and estimate the frequency of $o_i$ by their median.

Based on these two operations, the DSA outputs an estimate of the frequencies for the top k items. The DSA can be modified to work with a stream of terms by using a MurmurHash, which is a robust string hashing algorithm in the design of hash functions h and s. Other suitable hash function can also b used.

Returning to FIGS. 1A-1C, the results of the DreamNLP system is shown at 115 as a plot of the frequency of the terms where the term "breast" was most frequently used term and the term "imaging" was one of the least frequently used term.

The significance of each frequent term is evaluated by observing how these terms are distributed across different reports. The distribution can be quantitatively examined by using the Shannon entropy, which is denoted by H and defined as follows:

$$H = -\sum_{i=1}^{n} (p_i \log p_i)$$

Here n is the number of possible events and $p_i$ is the probability that i-th event occurs. If H attains its maximum value, it implies that all events are equally likely (i.e. $p_i$–1/n for all i). In the present context, the i-th event corresponds to a particular term appearing in the i-th report when there are n reports. Therefore, a high value of $H_T$, the Shannon entropy for a particular term T, implies that T appears in most of the reports while a low value implies that T only appears in a small subset of reports. Based on this property, $H_T$ can be used as a measure for T's usefulness, depending on the anticipated downstream task. The value $H_T$ is obtained by computing the values of $p_i$ as "$n_i/n_{total}$" where $n_i$ is the number of occurrences of T in the i-th report and $n_{total}$ is the total number of occurrences of T in the entire set of reports. Since there are at most k terms under consideration, the exact values of can be computed.

A visualization tool is used for viewing how the terms are actually distributed and used in the reports so that they can be better assessed for anticipated downstream tasks. Moreover, many different outputs can be generated for further data an or applications. At 120, a multi-distribution histogram of the terms with the records is show, where the x-axis is the clinical records, the y-axis is the significant words, and the z-axis-is the frequency of each term. The multi-dimensional histogram can be used to visualize and determine the relationship between frequencies, terms, and reports. At 125, the frequently used terms are shown traced back to theft actual used in the reports. At 130, an output of the neighboring words is generated for each term in a user defined format, which could be used for future post-processing or data analysis. For example, the amount of words to the left and right of a term can be configured to extract information associated with a string terms.

EXAMPLE

Clinical Database for Breast Imaging

Clinical reports of clinical encounters, pathology and imaging were obtained from patients who un dement breast imaging consisting of mammography, ultrasound, and MRI. For this study, all reports were anonymized with no patient health identifiers within the report. The reports were obtained by an approved IRB study following HIPPA criteria. Breast imaging reports are structured and must adhere to the Breast Imaging Reporting and Data System (BIRADS) format. Briefly, the BIRADs scoring gives a numerical index to the degree of potential malignancy of breast tumors. The BIRADS scale ranges from 1 to 6, where 1-3 is considered normal, 4-5 is considered highly suspicious and 6 is proven malignancy. Moreover, each breast is described by defined features, such as breast density, lesion shape, size, and distribution. Each clinical report was converted to a text file and read into the present system.

Imaging and non-imaging clinical reports were able to be distinguished and filter out non-BIRADS reports (a small number relative to BIRADS reports) as they contained terms with low Shannon entropy such as "FDG uptake" and were missing high entropy terms such as "BIRADS" and "assessment". Forty-six records (75%) out of the 61 reports available with BI-RADS reporting were selected and analyzed. The above-described processing was applied to 24,487 terms in the selected reports to extract the top 100 terms and it took about 20 milliseconds. The parameters t and b were chosen such that the results closely matched true values (i.e. t=20 and b=10,000). Careful analysis of the 100 terms revealed useful information on now to extract specific features from the BIRADS reports. Table 1 summarizes the analysis of the significant terms based on the entropy evaluation and context analysis.

TABLE 1

| BI-RADS reports extracted breast diagnosis features | | | |
|---|---|---|---|
| Dictionary Generation | Evaluation | Context Analysis | Insight Potential |
| Rank[1] Term(s) | Shannon Entropy[2] | Sample Neighboring Words | Feature |
| 5, 7 right breast, left breast | 94.38, 94.42 | RIGHT BREAST: LEFT BREAT: | Left/Right Distinction |
| 6 Cm | 89.33 | mass measuring 1.1 × 0.8 × 0.9 cm | Size of Lesion |
| 8 Mass | 83.65 | lobulated, spiculated mass | Type of Lesson |
| 13, 20 bi-rads, assessment | 84.69, 96.19 | BI-RADS 5: Highly suspicious . . . Assessment: 6 Known malignancy | BI-RADS Scores |
| 41, 95 o'clock, quadrant | 72.39, 70.58 | at the two o'clock position right upper outer quadrant | Site of Lesion |

TABLE 1-continued

BI-RADS reports extracted breast diagnosis features

| Dictionary Generation | | Evaluation | Context Analysis | Insight Potential |
|---|---|---|---|---|
| Rank[1] | Term(s) | Shannon Entropy[2] | Sample Neighboring Words | Feature |
| 34 | History | 92.81 | strong family history of breast cancer | Family history |
| 54, 74 | density, dense | 96.11, 86.34 | Breast density: Moderately dense. | Breast Density |

[1]The rank of a term based on its number of occurrences in the entire set of reports (estimated by Count Sketch algorithm).
[2]Percentage with respect to maximum possible value.

The high entropy values associated with each term indicate that these terms are more or less present in the majority of reports and thus can be used, information extraction and feature generation. For example, "BI-RADS Scores" were extracted from each report using the terms "BI-RADS", "Left or Right Breast", and "mass measuring", thus enabling the classification of patients into malignant or benign groups.

The example demonstrated that significant features related to breast diagnosis can be extracted from radiological clinical reports using key BIRADS features for improved diagnostic performance, while using very low computational memory and minimal prior knowledge of the structure of reports with high accuracy of correct extraction of terms. These selected terms then could be used for populating an "in house" corpora's from local populations for further informatics work. Besides the possibility of obtaining potential features, finding frequent terms can also reveal other useful insights from reports. For example, considering that most of the reports analyzed were malignant cases, the fact that the term "upper outer" appeared among the top 100 terms provides evidence that the upper outer quadrant of the breast is frequently vulnerable to carcinoma. These finding can be exploited to discover "hidden" connections between different variables or modalities and be integrated into the "big data" approach.

In certain instances, the frequent terms analysis might miss terms which appear consistently throughout many documents, but with relatively less frequency than other terms, such as "age" in the case of BI-RADS. However, this can be compensated by increasing the number of the top-k terms to find and filtering out more common words, such as, "be, to, as", and linking verbs.

Because narrative reports in medical records contain a wealth of information that may augment structured data for managing patient information and predicting trends in diseases, pertinent negatives are evident in text but are not usually indexed in structured databases. For example, the present system can determine whether a finding or disease mentioned within narrative medical reports is present or absent. As another example, a negative family history of a condition and/or disease may be a fact to consider for diagnosis and/or treatment.

Figure 3:
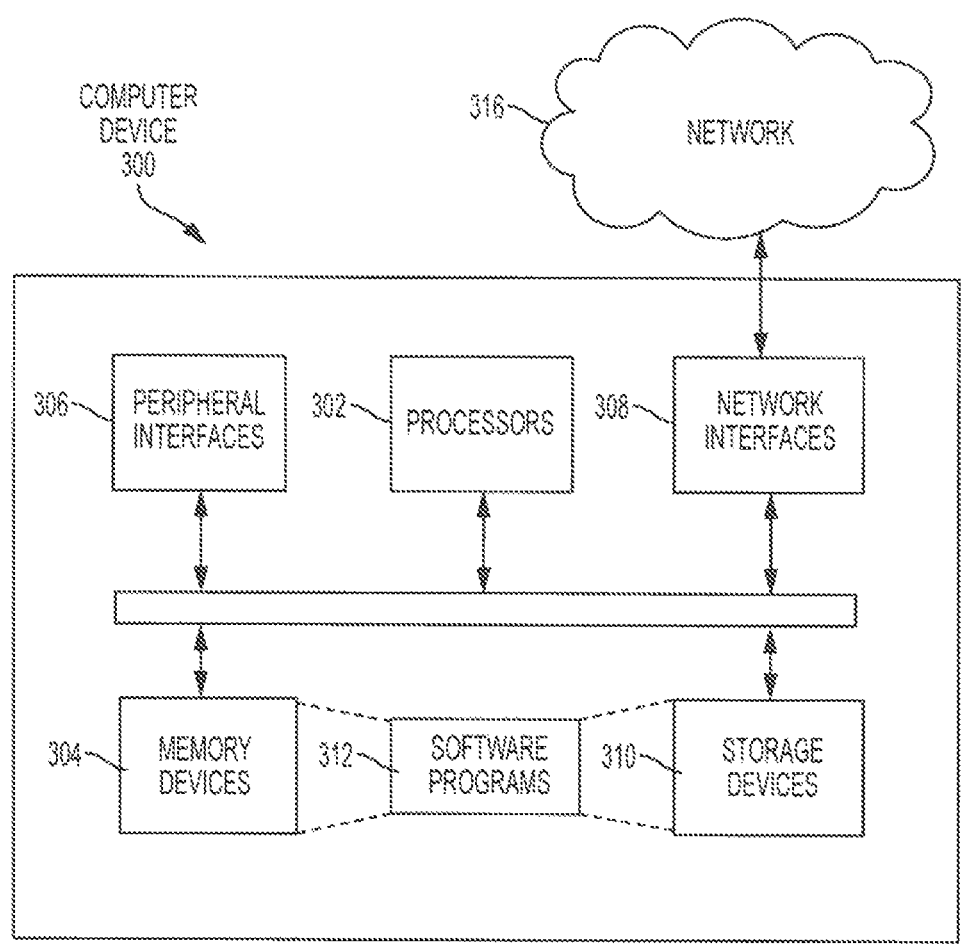
FIG. 3 is a diagram illustrating an example of a hardware system for performing at least a portion of one or more of the methods disclosed herein, according to examples of the present disclosure.

FIG. 3 illustrates an example of a hardware configuration for computer device 300 that can be used as mobile device or server, which can be used to perform one or more of the processes described above. While FIG. 3 illustrates various components contained in computer device 300, FIG. 3 illustrates one example of a computer device and additional components can be added and existing components can be removed.

Computer device 300 can be any type of computer devices, such as desktops, laptops, servers, etc., or mobile devices, such as smart telephones, tablet computers, cellular telephones, personal digital assistants, etc. As illustrated in FIG. 3, computer device 300 can include one or more processors 302 of varying core configurations and clock frequencies. Computer deice 300 can also include one or more memory devices 304 that serve as a main memory during the operation of computer device 300. For example, during operation, a copy of the software that supports the various processing described above, such as DREAMNLP, Shannon entropy, visualization, etc. can be stored in one or more memory devices 304. Computer device 300 can also include one or more peripheral interfaces 306, such as keyboards, mice, touchpads, computer screens, touchscreens, etc., for enabling human interaction with and manipulation of computer device 300.

The computer device 300 can also include one or more network interfaces 308 for communicating via one or more networks, such as Ethernet adapters, wireless transceivers, or serial network components, for communicating over wired or wireless media using protocols. The computer device 300 can also include one or more storage device 310 of varying physical dimensions and storage capacities, such as flash drives, hard drives, random access memory, etc., for storing data, such as images, files, and program instructions for execution by one or more processors 302.

Additionally, computer device 300 can include one or more software programs 312 that enable the functionality described above. One or more software programs 312 can include instructions that cause one or more processors 302 to perform the processes described herein. Copies of one or more software programs 312 can be stored in one or more memory devices 304 and/or on in one or more storage devices 310. Likewise, the data, for example, the DSA data utilized by one or more software programs 312 can be stored in one or more memory devices 304 and/or on in one or more storage devices 310.

In implementations, computer device 300 can communicate with other devices via network 316. The other devices can be any types t devices as described above. Network 316 can be any type of electronic network, such as a local area network, a wide area network, a virtual private network, the internet, intranet, an extranet, a public switched telephone network, fin infrared network, a wireless network, and any combination thereof. Network 316 can support communications using any of a variety of commercially available protocols, such as TCP/IP, UDP, OSI, FTP, UPnP, NFS, CIFS, AppleTalk, and the like. Network 316 can be, for example, a local area network, a wide-area network, a virtual private network, the Internet, an intranet, an extranet, a public switched telephone network, an infrared network, a wireless network, and any combination thereof.

Computer device 300 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers or other network devices may be stored locally and/or remotely, as appropriate.

In implementations, the components of computer device 300 as described above need not be enclosed within a single enclosure or even located in close proximity to one another. Those skilled in the art will appreciate that the above-described componentry are examples only, as computer device 300 can include any type of hardware componentry, including any necessary accompanying firmware or software, for performing the disclosed implementations. Computer device 300 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The foregoing description is illustrative, and variations in configuration and implementation can occur to persons skilled in the art. For instance, the various illustrative logics, logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration, In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

While the teachings have been described with reference to examples of the implementations thereof, those skilled in the art will be able to make various modifications to the described implementations without departing from the true spirit and scope. The terms and descriptions used herein are set forth by way of illustration only and are not meant as limitations. In particular, although the processes have been described by examples, the stages of the processes can be performed in a different order than illustrated or simultaneously. Furthermore, to the extent that the terms "including", "includes", "having", "has", "with", or variants thereof are used in the detailed description, such terms are intended to be inclusive in a manner similar to the term "comprising," As used herein, the terms one or more of and "at least one of" with respect to a listing of items such as, for example, A and B, means A alone, B alone, or A and B. Further, unless specified otherwise, the term "set" should be interpreted as "one or more." Also, the term "couple" or "couples" is intended to mean either an indirect or direct connection. Thus, if a first device couples to a second device, that connection can be through a direct connection, or through an indirect connection via other devices, components, and connections.

Those skilled in the art will be able to make various modifications to the described embodiments without departing from the true spirit and scope. The terms and descriptions used herein are set forth by way of illustration only and are not meant as limitations, in particular, although the method has been described by examples, the steps of the method can be performed in a different order than illustrated or simultaneously. Those skilled in the art will recognize that these and other variations are possible within the spirit and scope as defined in the following claims and their equivalents.

The foregoing description of the disclosure, along with its associated embodiments, has been presented for purposes of illustration only. It is not exhaustive and does not limit the disclosure to the precise form disclosed. Those skilled in the art will appreciate from the foregoing description that modifications and variations are possible in light of the above teachings or may be acquired from practicing the disclosure. For example, the steps described need not be performed in the same sequence discussed or with the same degree of separation. Likewise various steps may be omitted, repeated, or combined, as necessary, to achieve the same or similar objectives. Similarly, the systems described need not necessarily include ail parts described in the embodiments, and may also include other pars not describe in the embodiments.

Accordingly, the disclosure is not limited to the above-described embodiments, but instead is defined by the appended claims in light of their full scope of equivalents.

What is claimed is:

1. A method of obtaining frequent terms in a set of data, the method comprising:
   obtaining the set of data comprising a stream of terms;
   filtering the stream of terms to remove a preselected list of common words and linking verbs to produce a filtered stream of terms;
   analyzing the filtered stream of terms using a modified data streaming generator, wherein the modified data streaming generator comprises a hash function to find a set of frequent terms and an accuracy of each frequent term in the set of frequent terms, wherein the analyzing comprises parsing the set of data to identify syntactic relations, sematic relations, or both between terms and testing an entropy or mutual information of each term in the stream of terms that was parsed in relationship to a frequency, a position, and importance;
   forming a dictionary of terms based on the set of frequent terms;
   identifying one or more of the set of frequent terms in the set of data;
   analyzing the one or more of the set of frequent terms in the set of data to determine a context and/or structure based on neighboring terms in the set of data;
   generating a multidimensional graphic visualization tool for visualizing the stream of terms based on the analyzing; and
   displaying the multidimensional graphic visualization on a display device.

2. The method of claim 1, wherein a term from the stream of terms comprising a single word or a sequential set of words.

3. The method of claim 1, wherein the set of data comprises data from one or more data sources.

4. The method of claim 1, wherein subsequent to the obtaining, the method further comprises converting the stream of terms into a plurality of input vectors by the modified data streaming generator.

5. The method of claim 4, wherein subsequent to the converting the stream of terms, the method further comprises converting the plurality of input vectors into a corresponding plurality of sketch feature vectors by the data streaming generator, wherein each of the plurality of sketch feature vectors has a number of output dimensions that is less than a number of dimensions of a corresponding one of the input vectors.

6. The method of claim 1, further comprising determining Shannon entropy to evaluate a distribution of the terms across the set of data.

7. The method of claim 1, further comprising generating a multidimensional histogram to show interrelationships between terms of the stream of terms.

8. The method of claim 1, wherein the set of data comprises a scientific or financial corpus of data.

9. The method of claim 1, wherein the analyzing the stream of terms, further comprises extracting negations and determining a structure surrounding the negation.

10. The method of claim 1, further comprising storing the one or more of the set of frequent terms in a data store for further analysis.

11. A system comprising:
   one or more processors; and
   a memory system comprising one or more non-transitory computer-readable media storing instructions that, when executed by at least one of the one or more processors, cause the one or more processors to perform a method of obtaining frequent terms in a set of data, the method comprising:
   obtaining the set of data comprising a stream of terms;
   filtering the stream of terms to remove a preselected list of common words and linking verbs to produce a filtered stream of terms;
   analyzing the filtered stream of terms using a modified data streaming generator, wherein the modified data streaming generator comprises a hash function to find a set of frequent terms and an accuracy of each frequent term in the set of frequent terms, wherein the analyzing comprises parsing the set of data to identify syntactic relations, sematic relations, or both between terms and testing an entropy or mutual information of each term in the stream of terms that was parsed in relationship to a frequency, a position, and importance;
   forming a dictionary of terms based on the set of frequent terms;
   identifying one or more of the set of frequent terms in the set of data; and
   analyzing the one or more of the set of frequent terms in the set of data to determine a context and/or structure based on neighboring terms in the set of data;
   generating a multidimensional graphic visualization tool for visualizing the stream of terms based on the analyzing; and
   displaying the multidimensional graphic visualization on a display device.

12. The system of claim 11, wherein a term from the stream of terms comprising a single word or a sequential set of words.

13. The system of claim 11, wherein the set of data comprises data from one or more data sources.

14. The system of claim 11, wherein subsequent to the obtaining, the method further comprises converting the stream of terms into a plurality of input vectors by the modified data streaming generator.

15. The system of claim 14, wherein subsequent to the converting the stream of terms, the method further comprises converting the plurality of input vectors into a corresponding plurality of sketch feature vectors by the data streaming generator, wherein each of the plurality of sketch feature vectors has a number of output dimensions that is less than a number of dimensions of a corresponding one of the input vectors.

16. The system of claim 11, wherein the one or more processors are configured to further perform the method comprising determining Shannon entropy to evaluate a distribution of the terms across the set of data.

* * * * *